US007018660B2

(12) United States Patent
Murad

(10) Patent No.: US 7,018,660 B2
(45) Date of Patent: *Mar. 28, 2006

(54) PHARMACEUTICAL COMPOSITIONS AND METHODS FOR MANAGING SKIN CONDITIONS

(75) Inventor: Howard Murad, 4265 Marina City Dr., Penthouse 11, Marina del Ray, CA (US) 90292

(73) Assignee: Howard Murad, Marina del Ray, CA (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/093,443

(22) Filed: Mar. 11, 2002

(65) Prior Publication Data

US 2002/0172719 A1 Nov. 21, 2002

Related U.S. Application Data

(60) Division of application No. 09/878,231, filed on Jun. 12, 2001, now Pat. No. 6,383,523, which is a continuation of application No. 09/549,202, filed on Apr. 13, 2000, now Pat. No. 6,296,880, which is a continuation-in-part of application No. 09/330,127, filed on Jun. 11, 1999, now Pat. No. 6,071,541.

(60) Provisional application No. 60/094,775, filed on Jul. 31, 1998.

(51) Int. Cl.
*A61K 33/40* (2006.01)
*A61K 31/35* (2006.01)
*A61K 31/495* (2006.01)

(52) U.S. Cl. ............ 424/616; 514/248; 514/739; 514/460

(58) Field of Classification Search ............ 424/616; 514/248, 739, 460
See application file for complete search history.

(56) References Cited

U.S. PATENT DOCUMENTS

| 3,297,456 A | 1/1967 | Newell | 106/3 |
|---|---|---|---|
| 4,051,058 A | 9/1977 | Bowing et al. | 252/186 |
| 4,051,059 A | 9/1977 | Bowing et al. | 252/186 |
| 4,203,765 A | 5/1980 | Claeys et al. | 430/252 |
| 4,438,102 A * | 3/1984 | Ganci | 424/616 |
| 4,534,945 A | 8/1985 | Hopkins et al. | 423/273 |
| 4,557,935 A | 12/1985 | af Ekenstam et al. | 424/130 |
| 4,900,721 A * | 2/1990 | Bansemir et al. | 514/25 |
| 5,008,030 A | 4/1991 | Cook et al. | 510/384 |
| 5,139,788 A * | 8/1992 | Schmidt | 424/616 |
| 5,177,099 A | 1/1993 | Rovati et al. | 514/399 |
| 5,296,215 A | 3/1994 | Burke et al. | 424/49 |
| 5,357,636 A | 10/1994 | Dresdner, Jr. et al. | 2/161.7 |
| 5,519,059 A | 5/1996 | Sawaya | 514/599 |
| 5,547,990 A | 8/1996 | Hall et al. | 514/563 |
| 5,593,952 A | 1/1997 | Jarrett | 507/131 |
| 5,641,475 A | 6/1997 | Yu et al. | 424/65 |
| 5,693,318 A | 12/1997 | Burke et al. | 424/78.02 |
| 5,695,745 A | 12/1997 | Barton et al. | 424/49 |
| 5,861,432 A | 1/1999 | Sklar | 514/557 |
| 5,869,062 A | 2/1999 | Oliver | 424/195.1 |
| 5,951,993 A * | 9/1999 | Scholz et al. | 424/405 |
| 5,958,984 A | 9/1999 | Devillez | 514/714 |
| 6,071,541 A * | 6/2000 | Murad | 424/616 |
| 6,296,880 B1 * | 10/2001 | Murad | 424/616 |
| 6,383,523 B1 * | 5/2002 | Murad | 424/616 |

FOREIGN PATENT DOCUMENTS

| CA | 1 174 976 | 9/1984 |
|---|---|---|
| EP | 0 191 214 A2 | 8/1986 |
| EP | 2 250 539 B1 | 5/1991 |
| EP | 0 425 507 B1 | 2/1995 |
| GB | 1135643 | 12/1968 |
| GB | 2 076 286 A | 12/1981 |
| GB | 2 189 394 B | 10/1987 |

OTHER PUBLICATIONS

Nelson et al., Cyclodextrins in dental products, Database USPATFUL, USpatent 5945087(relative portion provided), 1999.*
Derbelmas-Lorentz, The anthelmintic action of essential oil . . . , Database CAPLUS, AN 1955:40866, abstract only, 1955, vol. 5 pp. 2-51.*
Savchenko., Testing of the anthelmintic action . . . , Database CAPLUS, AN 1954:61527, abstract only, 1954, pp. 84-88.*
Hashimoto Y.,ANthelmintics. II, Comparison . . . , Database CAPLUS, 1953:23039, abstract only, 1952, vol. 48(1), pp. 52-64.*
Ashikaga, M., Synthetic anthelmintics I., . . . , Database CAPLUS, AN 1958:57524, abstract only, 1954, vol. 66, pp. 965-975.*
CAius, et al., THe correlation between the chemical . . . , Database CAPLUS, AN 1924:11214, abstract only, 1923, vol. 11, pp. 371-375.*
Zheng, L., Multi-function, long acting . . . , Database CAPLUS, AN 1995:789385, Chinese Patent CN 1100331 (1995), abstract only.*

(Continued)

*Primary Examiner*—Vickie Kim
(74) *Attorney, Agent, or Firm*—Kenyon & Kenyon LLP

(57) ABSTRACT

This application relates to a stable pharmaceutical composition and methods for the cleansing of skin to facilitate the prevention, treatment, and management of skin conditions, such as seborrheic dermatitis, psoriasis, folliculitis, rosacea, perioral dermatitis, acne, impetigo and other inflammatory skin conditions, and the like, including a sufficient amount of an acidic component of a hydroxyacid or tannic acid, or a pharmaceutically acceptable salt thereof, to exfoliate a portion of the skin, a sufficient amount of stabilized hydrogen peroxide to facilitate cleansing of the skin without substantial irritation thereof, and an antimicrobial agent including at least one of an antibacterial agent, antimicrobial agent, antiviral agent, anthelmintic, or a combination thereof, in an amount sufficient to inhibit or reduce microorganisms on the skin.

9 Claims, No Drawings

OTHER PUBLICATIONS

Delli Santi et al., Database USPATFUL, USpatent 5945088 (1999), relative portion provided.*

De Grandis et al., Undecylenic Acid Derivatives for the Treatment of Mycosis . . . , abstract, Rib. ital. Essenze, profumi, . . . , 1974, vol. 56(7), pp. 371-379.s.

Mills, O.H., Jr. and Kligman, A.M., "Therapeutic Options in the Management of Acne and its Variants," Semin. Dermatol., pp. 233-237, 1982.

Sioufi et al., "GLC determination of free and conjugated triclosan in human plasma and urine," J. of Pharm. Sciences, vol. 66/8, pp. 1166-1168, 1977.

Wile et al., Hexetidine ('Oraldene'): a report on . . . , abstract, Current Med. Res. Opin, 1986, vol. 10(2), pp. 82-88.

* cited by examiner

PHARMACEUTICAL COMPOSITIONS AND METHODS FOR MANAGING SKIN CONDITIONS

CROSS REFERENCE TO RELATED APPLICATIONS

This application is a divisional of application Ser. No. 09/878,231, filed Jun. 12, 2001, now allowed; now U.S. Pat. No. 6,383,523 which is a continuation of application Ser. No. 09/549,202, filed Apr. 13, 2000, currently U.S. Pat. No. 6,296,880, which is continuation-in-part of application Ser. No. 09/330,127, filed Jun. 11, 1999, currently U.S. Pat. No. 6,071,541, which is a continuation-in-part of provisional application No. 60/094,775, filed Jul. 31, 1998.

TECHNICAL FIELD

This application relates to pharmaceutical compositions and methods to cleanse skin and facilitate the prevention, treatment, and management of skin conditions.

BACKGROUND OF THE INVENTION

Human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the micro-relief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by, for example, dryness, yeast, and structural changes in the skin, such as due to aging and excessive sun exposure.

Various pharmaceuticals have been used for the treatment or prevention of skin conditions, including skin cleansing compositions. Some of these compositions are discussed below.

Canadian Patent No. 1,174,976 discloses a germ-killing skin medication including two gels to be applied and mixed in situ, the first gel having sodium chlorite in an aqueous form and the second gel having lactic acid in an aqueous gel.

Great Britain Application No. 2,076,286 A discloses a dermatological composition of an oil medium dispersed in an aqueous medium that contains hydrogen peroxide, a buffer to maintain the composition below a pH of 7, and a starch gelled in situ. The buffer may include lactic, citric, tartaric, maleic, or hydroxysuccinic acids with an acid salt.

Great Britain Application No. 2,189,394 A discloses a concentrate that can be mixed with hydrogen peroxide to become an effective disinfectant for water, foodstuff, animal feeds, equipment, packages, and the like. The concentrate includes an inorganic acid with a pH less than 1.6, a silver compound or colloidal silver, an organic acid stabilizer such as tartaric, lactic, salicylic, or citric acid, and optionally gelatin.

European Patent Application No. 0,191,214 A2 discloses a cosmetic liquid cleanser for treating blemished, scarred, or inflamed skin having boric acid or borax, ammonium hydroxide, a peroxide, and optionally salicylic acid.

European Patent No. 0,250,539 B1 discloses a stabilized aqueous hydrogen peroxide composition having 0.1 to 4 weight percent hydrogen peroxide and 0.5 to 5 weight percent β-crystals of one or more lipids selected from monoglycerides of fatty acids, ascorbic acid, phosphate or lactic acid esters of fatty acids and monoglycerol ethers, said fatty acids and ether chains being saturated and having 12 to 18 carbons.

European Patent No. 0,425,507 B1 discloses compositions for treating abnormal or damaged conditions of the epithelium including skin, which include 0.01 to 12 weight percent of an activated protein containing at least 0.5 weight percent cysteine, 0.1 to 15 weight percent of a reducing agent to reduce cystine to cysteine, and 81.0 to 99.889 weight percent water, acids, bases, buffering agents, emulsifying agents, thickeners, solvents, preservatives, coloring agents, and perfuming agents. The reducing agent may be a salt of a thioglycolic acid. In a preferred embodiment, the composition also includes an oxidizing agent, such as hydrogen peroxide.

U.S. Pat. No. 3,297,456 discloses cleaning and polishing compositions, particularly for floor waxing, having lactic acid, methanol, hydrogen peroxide, and aqua ammonia in a particular ratio.

U.S. Pat. Nos. 4,015,058 and 4,015,059 disclose stable peroxy-containing concentrates useful for the production of microbicidal agents consisting essentially of an aqueous mixture of 0.5 to 20 weight percent peracetic or perpropionic acid or their precursors, 25 to 40 weight percent hydrogen peroxide, and optionally up to 5 weight percent anionic surface-active compounds of the sulfonate and sulfate type. Also disclosed are compositions that further include 0.25 to 10 weight percent organic phosphonic acid capable of sequestering bivalent metal cations and their water-soluble acid salts.

U.S. Pat. No. 4,203,765 discloses an aqueous acidic etch-bleach solution of hydrogen peroxide, iron ions, and inorganic anions that form a silver salt, such that in the dissolved state the solution contains citric acid and a polymer of alkylene oxide units for stabilization of the hydrogen peroxide.

U.S. Pat. No. 4,438,102 discloses compositions containing gelatin, hydrogen peroxide, ammonium hydroxide, thioglycolic acid, and a lower alkanol to promote the growth of dermal and epidermal tissue.

U.S. Pat. No. 4,534,945 discloses an aqueous 25 to 35 weight percent solution of hydrogen peroxide stabilized against decomposition with up to 1.4 mg/L tin, which is maintained in solution by particular amounts of phosphate in the form of phosphonic acid and hydroxycarboxylic acid.

U.S. Pat. No. 4,557,935 discloses a germicidal composition of hydrophilic lipid crystals of 1-monolaurin, and preferably 1-monomyristin, and hydrogen peroxide, whereby the former stabilize the latter. Optionally, the compositions further contain salicylic acid.

U.S. Pat. No. 4,900,721 discloses liquid, aqueous disinfectants based on alcohol and hydrogen peroxide that contain one or more $C_{2-8}$ alcohols, hydrogen peroxide or a hydrogen peroxide forming compound, one or more carboxylic acids, one or more microbicidally active nitrogen-containing organic compounds, one or more microbicidally active phenolic compounds for disinfection of the skin and mucous membrane.

U.S. Pat. No. 5,139,788 discloses an antimicrobial surface sanitizing composition having a diluent and antimicrobial agent of an antimicrobially effective amount of alpha-hydroxyacid substituted mono- or di-carboxylic acid and an antimicrobially effective amount of hydrogen peroxide, such that the composition leaves a non-contaminating residue after contact with surfaces to be disinfected.

U.S. Pat. No. 5,693,318 discloses phosphate esters for the improvement of water solubility of salicylic acid and peroxide compounds in an aqueous cleanser.

Despite these references, a stable composition of hydrogen peroxide, a hydroxy acid, and an antimicrobial agent has not been prepared and used for cleansing skin and managing skin conditions. Thus, there is still a need for improved pharmaceutical compositions and methods capable of cleansing the skin to facilitate the prevention, treatment, and management of skin conditions, such as folliculitis, seborrheic dermatitis, psoriasis, rosacea, perioral dermatitis, acne, impetigo and other inflammatory skin conditions, and the like. The present invention advantageously provides pharmaceutical compositions and methods for cleansing skin to facilitate the prevention, treatment, and management of one or more skin conditions.

SUMMARY OF THE INVENTION

The present invention relates to a skin cleansing pharmaceutical composition, preferably for administration to a patient, including an acidic component having a hydroxy acid or tannic acid, or a pharmaceutically acceptable salt thereof, in an amount sufficient to exfoliate at least a portion of the skin, hydrogen peroxide in an amount sufficient to cleanse the skin without substantial irritation thereof, and an antimicrobial agent including at least one of an antibacterial agent, an antifungal agent, an antiviral agent, an anthelmintic, or a combination thereof, in an amount sufficient to at least inhibit microorganisms on the skin. In a preferred embodiment, the composition further includes a pharmaceutically acceptable carrier or excipient.

In one embodiment, the acidic component includes an alpha-hydroxy acid, beta-hydroxy acid, or tannic acid. In a preferred embodiment, the acidic component includes glycolic acid, lactic acid, citric acid, salicylic acid, or tannic acid.

Advantageously, the acidic component is present in an amount from about 0.1 to 8 weight percent, the hydrogen peroxide is present in an amount from about 0.01 to 6 weight percent, and the antimicrobial agent is present in an amount from about 0.01 to 1.5 weight percent of the composition. In a preferred embodiment, the composition further includes at least one of a surfactant, a stabilizer, a preservative, a moisturizer, anti-inflammatory agent, anti-oxidant, and a coloring agent, which together may be present in an amount from about 10. 1 to 99.1 weight percent of the composition.

The acidic component can include an amount of citric acid sufficient to inhibit hydrogen peroxide decomposition over at least three months. In a more preferred embodiment, the amount of citric acid is sufficient to inhibit hydrogen peroxide decomposition at 40° C. over at least three months. The invention also relates to a gel, paste, cream, lotion, emulsion, or ointment that includes these pharmaceutical compositions.

In one preferred embodiment, the antimicrobial agent includes an antifungal agent. In a more preferred embodiment, the antifungal agent is selected from the group of farnesol, clotrimazole, ketoconazole, econazole, fluconazole, calcium or zinc undecylenate, undecylenic acid, butenafine hydrochloride, ciclopirox olaimine, miconazole nitrate, nystatin, sulconazole, terbinafine hydrochloride, and mixtures thereof.

In another preferred embodiment, the antimicrobial agent includes an antibacterial agent. In a more preferred embodiment, the antibacterial agent is selected from the group of triclosan, neomycin, clindamycin, polymyxin, bacitracin, benzoyl peroxide, a tetracycline such as doxycycline or minocycline, a sulfa drug such as sulfacetamide, a penicillin, a cephalosporin such as cephalexin, a quinolone such as lomefloxacin, olfloxacin, or trovafloxacin, and mixtures thereof.

In yet another preferred embodiment, the antimicrobial agent includes an antiviral agent. In a more preferred embodiment, the antiviral agent is selected from the group of acyclovir, tamvir, penciclovir, and mixtures thereof.

The invention further relates to a method of managing a skin condition by administering to a patient a therapeutically effective amount of: (1) an acidic component including a hydroxy acid or tannic acid, or a pharmaceutically acceptable salt thereof, (2) hydrogen peroxide, and (3) an antimicrobial agent including at least one of an antibacterial agent, an antifungal agent, antiviral agent, an anthelmintic, or a combination thereof, to at least inhibit the growth of microorganisms on the skin that contributes to, or causes, the skin condition.

The types of skin conditions that can be treated include seborrheic dermatitis, psoriasis, folliculitis, rosacea, perioral dermatitis, acne, or impetigo or other inflammatory skin conditions. The administration of the components may be topical, such as by at least one of a gel, paste, cream, lotion, emulsion, or ointment. About 1 mg to 10,000 mg of the acidic component, hydrogen peroxide, and antimicrobial agent are administered together for satisfactory results in most cases. In a preferred embodiment, the acidic component, hydrogen peroxide, and antimicrobial agent are administered concurrently. In another embodiment, the acidic component, hydrogen peroxide, and antimicrobial agent are administered concurrently with at least one additional pharmaceutical composition for the prevention or treatment of a skin condition. In this embodiment, the method further includes administering at least one of a surfactant, stabilizer, preservative, moisturizer, anti-inflammatory agent, anti-oxidant, or coloring agent. Alternatively, the acidic component can include an alpha-hydroxy acid, beta-hydroxy acid, or tannic acid and the antimicrobial agent can include an antibacterial agent. In a more preferred embodiment, the acidic component includes glycolic, lactic, tannic, citric, or salicylic acid, and the antimicrobial agent includes triclosan.

The invention also relates to a skin cleansing pharmaceutical composition including an acidic component containing a hydroxy acid or tannic acid, or a pharmaceutically acceptable salt thereof, present in an amount greater than about 1 weight percent to exfoliate at least a portion of the skin, hydrogen peroxide in an amount sufficient to cleanse the skin without substantial irritation thereof, and an antimicrobial agent that essentially includes at least one of an antibacterial agent, antifungal agent, antiviral agent, an anthelmintic, or a combination thereof, in an amount sufficient to at least inhibit microorganisms on the skin.

DETAILED DESCRIPTION OF THE PREFERRED EMBODIMENTS

A formulation for the prevention, treatment, and management of skin conditions, such as seborrheic dermatitis, psoriasis, folliculitis, rosacea, perioral dermatitis, acne, impetigo and other inflammatory skin conditions, and the like, has now been discovered. Moreover, the management of these skin conditions may advantageously be accomplished by the administration of the pharmaceutical composition of the present invention.

The term "skin conditions," as used herein, means conditions present anywhere on the skin including seborrheic dermatitis, psoriasis, folliculitis, rosacea, perioral dermatitis, acne, impetigo and other inflammatory skin conditions, and the like.

The terms "managing" or "management," as used herein, includes one or more of the prevention, treatment, or modification of a skin condition.

The term "inhibit hydrogen peroxide decomposition," as used herein, means to at least stop the rate of decomposition from increasing, preferably to inhibit the decomposition entirely, and more preferably to substantially inhibit the decomposition altogether. "Substantially inhibit," as used herein, means that less than about 10 weight percent, preferably less than about 3 weight percent, and more preferably less than about 1 weight percent, of the hydrogen peroxide decomposes over a three month period of time.

Methods for administering the compositions herein are also encompassed by the invention. Such methods are used for the prevention, treatment, or management of one or more of: eczema, psoriasis, folliculitis, scaling, seborrhea or seborrheic dermatitis, rosacea, perioral dermatitis, acne, impetigo and other inflammatory skin conditions, all while substantially avoiding irritation to the skin. The compositions may be prepared in high concentrations for administration as a cleanser to be removed shortly thereafter, as well as in lower concentrations that are safer for products that can remain in contact with the skin for longer times.

The pharmaceutical compositions of the invention include the combination of a number of different components that interact to provide the desired management of the skin. The compositions include an acidic component including one or more mono- or poly-hydroxy acids or tannic acid, a mixture thereof, or a pharmaceutically acceptable salt or ester thereof. One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxypolycarboxylic acids. One of ordinary skill in the art would typically select one or more of the following mono- or poly-hydroxy acids:2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof; and 2-hydroxyphenyl pyruvic acid and esters thereof. The hydroxy acids are preferably selected from one or more alpha-hydroxy acids or beta-hydroxy acids, more preferably from glycolic, lactic, citric, tannic, or salicylic acid, and most preferably from citric and salicylic acids. It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370 are also suitable for use in the compositions and methods of the invention. The acidic component is present in the composition and methods in an amount sufficient to exfoliate, i.e., remove dead or dying skin cells, from at least a portion of the skin. The acidic component is typically present in an amount from about 0.1 to 12 weight percent, preferably about 1 to 11 weight percent, more preferably from about 4 to 10 weight percent of the composition. For example, the acidic component maybe from about 0.1 to 3 weight percent citric acid in combination with up to about 2 weight percent salicylic acid.

Compositions and methods for managing eczema, psoriasis, folliculitis, scaling, seborrhea or seborrheic dermatitis, rosacea, perioral dermatitis, acne, impetigo and other inflammatory skin conditions, and the like, also include hydrogen peroxide and an antimicrobial agent. The hydrogen peroxide is present in an amount sufficient to cleanse at least a portion of the skin. "Cleanse" as used herein includes the removal of dirt, debris, air pollutants, desquamating cells, and cutaneous secretions of the skin. The hydrogen peroxide is typically present in an amount from about 0.01 to 6 weight percent, preferably 0.05 to 4 weight percent, and more preferably 0.1 to 1 weight percent of the composition.

Any pharmaceutically acceptable antimicrobial agent available to those of ordinary skill in the art may be used, but preferably at least one of an antibacterial agent, antifungal agent, antiviral agent, or anthelmintic will be used according to the invention. A single broad spectrum antimicrobial agent, i.e., one that is believed to have at least two of antibacterial, antifungal, and antiviral efficacy, include: echinacea, golden seal, benzalkonium chloride, benzethonium chloride, iodine, grape seed extract, pomegranate extract, green tea extract or polyphenols, and the like, or combinations thereof, may be included. Another suitable antimicrobial agent includes the class of anthelmintics, such as metronidazole, to facilitate treatment of, e.g., tricomona infection. Preferred antiviral agents include, but are not limited to, acyclovir, tamvir, penciclovir, and the like, and mixtures thereof. Preferred antibacterial agents include, but are not limited to, triclosan, neomycin, polymyxin, bacitracin, clindamycin, benzoyl peroxide, a tetracycline, a sulfa drug, a penicillin, a quinolone, a cephalosporin, and mixtures thereof. Preferred antifungal agents include, but are not limited to, farnesol, econazole, fluconazole, clotrimazole, ketoconazole, calcium or zinc undecylenate, undecylenic acid, butenafine hydrochloride, ciclopirox olaimine, miconazole nitrate, nystatin, sulconazole, terbinafine hydrochloride, and the like, and mixtures thereof. Exemplary tetracyclines include doxycycline and minocycline. An exemplary sulfa drug includes sulfacetamde. An exemplary cephalosporin includes cephalexin (commercially available as KEFLEX). Exemplary quinolones include the floxacins, such as loemfloxacin, ofloxacin, and trovafloxacin. It should be readily understood that any salts, isomers, pro-drugs, metabolites, or other derivatives of these antimicrobial agents may also be included as the antimicrobial agent in accordance with the invention. The antimicrobial agent is typically present in an amount from about 0.01 to 1.5 weight percent, preferably from about 0.1 to 1.2 weight percent, and more preferably from about 0.3 to 1 weight percent of the composition. The antimicrobial agent inhibits the formation, and may further reduce, the presence of microbes that cause redness, inflammation, and irritation of the skin. Together, the acidic component, hydrogen peroxide, and antimicrobial agent facilitate exfoliation of dead skin, cleanse the skin, remove substances foreign to the skin, inhibit or reduce the presence of microorganisms, and generally facilitate management of skin conditions, such as seborrheic dermatitis, psoriasis, folliculitis, rosacea, perioral dermatitis, acne, impetigo and other inflammatory skin conditions, and the like.

In a preferred embodiment, the compositions further include one or more of *Arnica Montana* (a healing herb); any vitamin A source including retinyl palmitate or other retinyl esters, retinoic acid, or Retinol; and Vitamin K. These components facilitate the skin cleansing and management of skin conditions accomplished by the acidic component, hydrogen peroxide, and antimicrobial agent. The *Arnica Montana* facilitates skin healing and acts as an antiseptic and local anti-inflammatory, and, when used, is typically present in an amount from about 0.1 to 2 weight percent, preferably about 0.2 to 1 weight percent. The Retinol facilitates normal skin production, particularly epidermal normalization, and, when used, is typically present in an amount from about 0.01 to 6 weight percent, preferably about 0.1 to 5 weight percent. The Vitamin K inhibits or suppresses inflammation and bruising (i.e., acts as an anti-inflammatory and anti-bruising agent) and, when used, is typically present in an amount from about 0.01 to 1 weight percent, preferably from about 0.1 to 0.5 weight percent.

In a preferred embodiment, the compositions all contain one or more surfactants, stabilizers, preservatives, moisturizers, coloring agents, anti-inflammatory agents, anti-oxidants, water, acids, bases, buffering agents, emulsifying agents, thickeners, solvents, perfuming agents, and the like, and mixtures thereof. The water used is preferably deionized water. It should be understood that water includes the remainder of a given composition after other ingredients are determined. Although any pharmaceutically acceptable surfactant, stabilizer, preservative, moisturizer, coloring agent, acids, bases, buffering agents, emulsifying agents, thickeners, solvents, or perfuming agents may be used, certain compounds or mixtures are preferred as discussed below.

Preferred surfactants, including both the foaming and non-foaming type, include sodium laureth sulfate, sodium laureth-13 carboxylate, disodium laureth sulfosuccinate, disodium cocoamphodiacetate, and the like, and mixtures thereof. More preferably, at least one amphoteric surfactant is included in the composition, such as disodium cocoamphodiacetate. The amphoteric surfactant, in combination with citric acid, inhibits hydrogen peroxide decomposition. The surfactant component may be present in an amount from about 10 to 90 weight percent, preferably about 20 to 80, and more preferably about 30 to 70 weight percent of the composition.

A preferred stabilizer includes glycol stearate or PEG-150 distearate. The stabilizer, when used, is typically present in an amount from about 0.1 to 5 weight percent of the composition.

Preferred preservatives include tetrasodium ethylene-diamine tetraacetic acid (EDTA), methylparaben, benzophenone-4, methylchloroisothiazolinone, methylisothiazolinone, and the like, and mixtures thereof. Preservatives, when used, are typically present in an amount from about 0.01 to 6 weight percent, preferably about 0.05 to 4 weight percent, and more preferably from about 0.1 to 2 weight percent.

Preferred moisturizers include wheat protein (e.g., laurdimonium hydroxypropyl hydrolyzed wheat protein), hair keratin amino acids, sodium peroxylinecarbolic acid, panthenol, tocopherol (Vitamin E), dimethicone, and the like, and mixtures thereof. Sodium chloride may also be present, particularly when hair keratin amino acids are included as a moisturizer. Moisturizers, when used, are typically present in an amount from about 0.01 to 2 weight percent, preferably about 0.05 to 1.5 weight percent, more preferably from about 0.1 to 1 weight percent of the composition.

Preferred coloring agents include FD&C Green No. 3, Ext. D&C Violet No. 2, FD&C Yellow No. 5, FD&C Red No. 40, and the like, and mixtures thereof. The coloring agents, when used, are typically present in an amount from about 0.001 to 0.1 weight percent, and preferably from about 0.005 to 0.05 weight percent of the composition.

Preferred anti-inflammatory agents include any pharmaceutically acceptable compounds suitable for administration orally or topically, preferably at least one of aloe vera gel, aloe vera, licorice extract, pilewort, Canadian willow root, zinc, or allantoin, more preferably allantoin. The anti-inflammatory agents, when present, are used in an amount sufficient to inhibit or reduce inflammation, preferably in an amount from about 0.1 to 2 weight percent, preferably from about 0.3 to 1.5 weight percent, and more preferably from about 0.3 to 1 weight percent of the composition. It should be understood, with reference to managing skin conditions, that the anti-inflammatory agents facilitate inhibition or suppression of inflammation anywhere on the skin.

Anti-oxidants of both the enzymatic and non-enzymatic type may be included in the compositions and methods of the invention. For example, superoxide dismutase (SOD), catalase, and glutathione peroxidase are natural enzymatic anti-oxidants used by the body that may be supplemented with the compositions herein. Suitable non-enzymatic anti-oxidants include such as Vitamin E (e.g., tocopherol), Vitamin C (ascorbic acid), carotenoids, Echinacoside and caffeoyl derivatives, oligomeric proanthocyanidins or proanthanols (e.g., grape seed extract), silymarin (e.g., milk thistle extract, *Silybum marianum*), ginkgo biloba, green tea polyphenols, and the like, and mixtures thereof. Carotenoids are powerful anti-oxidants, and they include beta-carotene, canthaxanthin, zeaxanthin, lycopen, lutein, crocetin, capsanthin, and the like. Indeed, any pharmaceutically acceptable compounds suitable for administration orally or topically may be used as an anti-oxidant in the compositions. Preferably, the anti-oxidant component includes Vitamin E, Vitamin C, or a carotenoid. The anti-oxidant component, when used, is present in an amount sufficient to inhibit or reduce the effects of free-radicals at the scalp. The anti-oxidant component may be present in an amount from about 0.001 to 1 weight percent, preferably from about 0.01 to 0.5 weight percent of the composition.

The ranges of the components of the pharmaceutical composition may vary, but the active ingredients should be understood to add to 100 weight percent of the active pharmaceutical composition.

The term "therapeutically effective amount" means that amount of the pharmaceutical composition that provides a therapeutic benefit in the treatment, prevention, or management of one or more skin conditions.

The magnitude of a prophylactic or therapeutic dose of the composition in the acute or chronic management of skin conditions will vary with the severity of the condition to be treated and the route of administration. The dose, and perhaps the dose frequency, will also vary according to the age, body weight, and response of the individual patient. In general, a preferred topical daily dose range, in single or divided doses, for the conditions described herein should be from about 1 mg to 20,000 mg, more preferably about 2,000 mg to 16,000 mg, and most preferably about 6,000 mg to 10,000 mg of the active components (i.e., excluding excipients and carriers).

Those of ordinary skill in the art will also understand that topical effectiveness of pharmaceuticals requires percutaneous absorption and bioavailability to the target site. Thus, the compositions and methods of the invention require penetration through the stratum corneum into the epidermal layers, as well as sufficient distribution to the sites targeted for pharmacologic action.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The term "unit dose" is meant to describe a single dose, although a unit dose may be divided, if desired. About 1 to 2 unit doses of the present invention are typically administered per day, preferably about 1 dose per day.

Any suitable route of administration may be employed for providing the patient with an effective dosage of the composition according to the methods of the present invention, including oral, intraoral, rectal, parenteral, topical, epicutaneous, transdermal, subcutaneous, intramuscular, intranasal, sublingual, buccal, intradural, intraocular, intrarespiratory, or nasal inhalation and like forms of administration. Topical administration is generally preferred for the compositions and methods of the invention. Suitable dosage forms include dispersions, suspensions, solutions, aerosols, sponges, cotton applicators, and the like, with topical dosage forms such as shampoos being preferred.

The pharmaceutical compositions used in the methods of the present invention include the active ingredients described above, and may also contain pharmaceutically acceptable carriers, excipients and the like, and optionally, other therapeutic ingredients.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucoronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

The compositions for use in the methods of the present invention may include components such as suspensions, solutions and elixirs; aerosols; or other suitable carriers such as starches, sugars, microcrystalline cellulose, diluents, granulating agents, lubricants, binders, disintegrating agents, and the like, with the topical preparations being preferred.

Because of its ease of administration, a cream, lotion, or ointment represents the most advantageous topical dosage unit form, in which case liquid pharmaceutical carriers may be employed in the composition. These creams, lotions, or ointments, may be prepared as rinse-off or leave-on products, as well as two stage treatment products for use with other skin cleansing or managing compositions. In a preferred embodiment, the compositions are administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention.

Pharmaceutical compositions for use in the methods of the present invention suitable for topical administration may be presented as discrete units including aerosol sprays, each containing a predetermined amount of the active ingredient, as a powder, stick, or granules, as creams (e.g., a conditioner), pastes, gels, lotions (e.g., a sunscreen), syrups, or ointments, on sponges or cotton applicators, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier(s) with the active ingredient, which constitutes one or more necessary ingredients. In general, the compositions are prepared by uniformly and intimately admixing the active ingredient with liquid carriers or finely divided solid carriers or both, and then, if necessary, shaping the product into the desired presentation.

Other suitable dosage forms include tablets, troches, capsules, patches, gel caps, magmas, lozenges, plasters, discs, suppositories, nasal or oral sprays, and the like. When an oral dosage unit form is used instead of the preferred topical dosage form, tablets, capsules, and gel caps are preferred, in which case solid pharmaceutical carriers may be employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are expressly incorporated herein by reference thereto.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

Desirably, each unit dose, e.g., gel, cream, or ointment, contains from about 1 mg to 2,000 mg of the active ingredient, preferably about 200 mg to 1,600 mg, and more preferably about 600 mg to 1,000 mg of the composition.

EXAMPLES

The invention is further defined by reference to the following examples describing in detail the preparation of the compound and the compositions used in the methods of the present invention, as well as their utility. The examples are representative, and they should not be construed to limit the scope of the invention.

Example 1

Skin Cleanser Formulation

A pharmaceutical composition according to the invention may be prepared for cleansing skin as set forth below:

| Ingredient | Trade Name/Supplier | % by Weight |
|---|---|---|
| Part A | | |
| Deionized Water | N/A | 49.2 |
| Trisodium Ethylene-Diamine-Tetraacetic Acid (EDTA) | HAMP-ENE Na₃T/Akzo Nobel | 0.2 |
| Sodium Laureth-13 Carboxylate | SURFINE WLL/Finetex | 10 |
| Disodium Laureth Sulfosuccinate | MACKANATE EL/McIntyre Group | 17 |
| Disodium Cocoamphodiacetate | MONATERIC CDX-38/Mona | 11 |
| PEG-150 Pentaerythrityl Tetrastearate | CROTHIX/Croda | 1.5 |
| PEG-150 Distearate | KESSCO PEG 6000 DS/Stepan | .7 |
| Methylparaben | N/A | 0.2 |
| Part B | | |
| Salicylic Acid | Salicylic Acid, powder, USP/Spectrum | 1.6 |
| Citric Acid | N/A | 1.5 |
| Triclosan | IRGASAN DP300/Ciba | 0.3 |
| Part C | | |
| PPG-26-Buteth-26, PEG-40 Hydrogenated Castor Oil | SOLUBILISANT LR1/Les Colorant Wackherr SA | 2 |
| Fragrance (Parfum) | Fragrance-BELL #J7393/Bell Flavors and Fragrances | 0.3 |
| Menthol | Menthol Crystals, USP | 0.1 |
| Part D | | |
| Butylene Glycol, Deionized water, Black Cohosh (*Cimicifuga Racemosa*) Extract | ACTIPHYTE OF BLACK SNAKEROOT BG50/Active Organics | 0.1 |
| Butylene Glycol, Deionized water, *Camellia Oleifera* Extract | ACTIPHYTE OF JAPANESE GREEN TEA BG50/Active Organics | 0.1 |
| Sodium Peroxylinecarbolic Acid (PCA) | AJIDEW-50/Ajinomoto | 0.2 |
| Cocamidopropyl PG-Dimonium Chloride Phosphate | PHOSPHOLIPID PTC/Mona | 1 |
| Part E | | |
| Hydrogen Peroxide | Hydrogen Peroxide, 35% solution, technical | 3 |
| | | 100% |

HAMP-ENE Na₃T is commercially available from Akzo Nobel Inc. of Dobbs Ferry, NY;
SURFINE WLL is commercially available from Finetex, Inc. of Elmwood Park, NJ;
MACKANATE EL is commercially available from McIntyre Group of University Park, IL;
MONATERIC CDX-38 and PHOSPHOLIPID PTC are commercially available from Mona Industries Inc. of Patterson, NJ;
CROTHIX is commercially available from Croda Inc. of Parsippany, NJ;
KESSCO PEG 600 DS is commercially available from Stepan Co. of Northfield, IL;
IRGASAN DP300 is commercially available from Ciba Specialty Chemicals Corp. of Albemarle, NC;
SOLUBILISANT LR1 is commercially available from Les Colorant Wackherr SA of St. Ouen L'Aumone, France;
BELL #J7393 is commercially available from Bell Flavors and Fragrances of Northbrook, IL;
ACTIPHYTE OF BLACK SNAKEROOT BG50 and ACTIPHYTE OF JAPANESE GREEN TEA BG50 are commercially available from Active Organics of Dallas, TX; and
AJIDEW –50 is commercially available from Ajinomoto USA Inc. of Teaneck, NJ.

Deionized water was metered into the processing tank and mixing subsequently begun. The water was heated to 75° C. and the remainder of Part A was added and mixed until uniform. The mixture was cooled to 60° C. and the Part B ingredients were added and mixed until uniform. The mixture was then cooled to 50° C. In a separate vessel, Part C was premixed until uniform and then added to the mixture of Parts A and B. Parts A, B, and C were mixed until uniform and cooled to 40° C. The Part D ingredients were added and mixed until uniform, then cooled to 30° C. Part E was added and mixed until uniform, resulting in a colorless, clear, slightly viscous fluid having a pH at 25° C. of between 4 to 4.5 and a viscosity between 3,000 to 4,000 cps (RVT: #4 @10 rpm @25° C.).

Example 2

Advanced Acne Prone Skin Formulation

A pharmaceutical composition according to the invention may be prepared for treating skin prone to acne as set forth below:

| Ingredient | Trade Name/Supplier | % by Weight |
|---|---|---|
| Part A | | |
| Deionized Water | N/A | 46.7 |
| Hydroxyethylcellulose | CELLOSIZE QP52,000H/Amerchol | 1 |

-continued

| Ingredient | Trade Name/Supplier | % by Weight |
|---|---|---|
| Part B | | |
| Tetrasodium Ethylene-Diamine-Tetraacetic Acid (EDTA) | HAMP-ENE 220/Akzo Nobel | 0.1 |
| Butylene Glycol | 1,3-butylene glycol/Ashland | 5 |
| Aloe Barbadensis Gel | Aloe Vera Freeze Dried Powder 200:1/Aloe | 0.1 |
| Methyl Gluceth-10 | GLUCAM E-10/Amerchol | 3 |
| Witch Hazel (*Hamamelis Virginiana*) Distillate | Witch Hazel Distillate, 14% | 3 |
| Zinc Acetate | Zinc Acetate, crystals, USP/FCC | 0.5 |
| Orange (*Citrus Aurantium Dulcis*) Extract Methylparaben | NATURAL ORANGE EXTRACT #71689/Flavurence | 0.3 |
| Dipotassium Glycyrrhizate | N/A | 0.3 |
| Lecithin, Tocopherol and Magnesium Ascorbyl Phosphate | OXYSOMES/Barnett | 0.3 |
| Palmitoyl Hydroxypropyltrimonium Amylopectin/Glycerin Crosspolymer, Lecithin, Grape (*Vitis Vinifera*) Seed Extract | GLYCOSPHERE PCO/Kobo | 0.2 |
| Palmitoyl Hydroxypropyltrimonium Amylopectin/Glycerin Crosspolymer, Lecithin, *Camellia Sinensis* Extract | GLYCOSPHERE GT/Kobo | 0.5 |
| *Epilobium Angustifolium* Extract | Canadian Willowherb Whole Extract (5% in water)/Fytokem | 0.5 |
| Butylene Glycol and Water and *Arnica Montana* Extract | ACTIPHYTE OF ARNICA BG50/Active Organics | 0.5 |
| Part C | | |
| Alcohol (denatured) | SD Alcohol 40-B, Anhydrous/ | 20 |
| Salicylic Acid | Salicylic Acid, powder, USP/FCC/Spectrum | 1 |
| Triclosan | IRGASAN DP300/Ciba | 0.4 |
| Part D | | |
| PPG-5-Ceteth-20 | PROCETYL AWS/Croda | 1 |
| PEG-40 Hydrogenated Castor Oil | CREMOPHOR RH-40/BASF | 0.6 |
| Retinol and Polysorbate 20 | RETINOL 50C/BASF | 0.1 |
| Phytonadione | N/A | 0.1 |
| Linoleic Acid | EMERSOL 315/Henkel | 0.3 |
| Part E | | |
| Glycolic Acid | GLYPURE = 70% Glycolic Acid/DuPont | 9 |
| Part F | | |
| Deionized water | N/A | 2 |
| Sodium Hydroxide | Sodium Hydroxide, pellets, USP/NF | 2 |
| Part G | | |
| Hydrogen Peroxide | Hydrogen Peroxide, 35% solution, technical | 1.5 |
| | | 100% |

CELLOSIZE QP52,000H and GLUCAM E-10 are commercially available from Amerchol Corp. of Edison, NJ;
HAMP-ENE 220 is commercially available from Akzo Nobel Inc. of Dobbs Ferry, NY;
Aloe Vera Freeze Dried Powder 200:1 is commercially available from Aloe Corp. of TX;
OXYSOMES is commercially available from Barnet Products Corporation of Englewood Cliffs, NJ;
Canadian Willowherb Whole Extract (5% in water) is commercially available from Fytokem, Inc. of Saskatoon, SK CANADA;
GLYCOSPHERE PCO and GLYCOSPHERE GT are commercially available from Kobo Products Inc. of South Plainfield, NJ;
ACTIPHYTE OF ARNICA BG50 is commercially available from Active Organics of Dallas, TX;
PROCETYL AWS is commercially available from Croda Inc. of Parsippany, NJ;
CREMOPHOR RH-40 and RETINOL 50C are commercially available from BASF Corporation of Budd Lake, NJ;
GLYPURE = 70% Glycolic Acid is commercially available from DuPont of Wilmington, DE;
EMERSOL 315 is commercially available from Henkel Corp. of Hoboken, NJ.

Deionized water was metered into the processing tank and mixing subsequently begun. CELLOSIZE QP52,000H was sprinkled in, heated to 70° C., and mixed until clear and uniform. The mixture was cooled to 40° C. Part B ingredients were added in the order above, with sufficient mixing after each ingredient was added. The mixture was cooled to 25° C. and premixed Part C ingredients were added and mixed until uniform. In a separate tank, Part D was heated to 40° C. until the solids were dissolved and then added to the batch of Parts A, B, and C. The mixture was mixed until uniform, then Part E was added and mixed until uniform. Premixed Part F was slowly added in increments as needed to obtain the desired pH of 3.3 to 3.8 at 25° C., then Part G was added and mixed until completely uniform. This resulted in a straw-colored, clear to slightly hazy, slightly viscous liquid having a pH @25° C. of 3.3 to 3.8 and a viscosity between 400 to 800 cps (RVT: #2 @10 rpm @25° C.).

Example 3

Skin Perfecting Lotion

A pharmaceutical composition according to the invention may be prepared for treating skin as set forth below:

| Ingredient | Trade Name/Supplier | % by weight |
|---|---|---|
| Part A | | |
| Water (Aqua) | Deionized water | 63.6 |
| Carbomer | CARBOPOL ULTREZ 10/B. F. Goodrich | 0.3 |
| Sclerotium Gum | AMIGEL/Tri-K | 0.6 |
| Glycerin | Glycerin 99.5%/Ashland | 6.0 |
| Butylene Glycol | 1,3-butylene glycol/Ashland | 6.0 |
| Allantoin | Allantoin/ISP | 0.6 |
| Panthenol | DEXPANTHENOL/Roche | 0.6 |
| Tetrasodium EDTA | HAMP-ENE 220/Akzo | 0.2 |
| Methylparaben | Methylparaben/Ueno | 0.3 |
| Sodium PCA | AJIDEW-50/Ajinomoto | 0.5 |
| Part B | | |
| Dicapryl Maleate | BERNEL ESTER DCM/Bernel | 6.0 |
| Squalene | PHYTOLANE/Barnet | 0.8 |
| Sorbitan Stearate | ARLACEL 60/ICI | 1.5 |
| Stearic Acid | EMERSOL 132/Henkel | 1.3 |
| Dimethicone | DOW CORNING 200, 350 cs./Dow Corning | 0.8 |
| C12–C15 Alkyl Benzoate | FINSOLV TN/Finetex | 3.0 |
| Cetearyl Alcohol and Ceteareth | HEXOTOL D/Heterene | 0.6 |
| Propylparaben | Propylparaben/Ueno | 0.2 |
| Part C | | |
| Water (Aqua) | Deionized water | 0.3 |
| Triethanolamine | Triethanolamine 99%/Ashland | 0.3 |

-continued

| Ingredient | Trade Name/Supplier | % by weight |
|---|---|---|
| Part D | | |
| Orange (*Citrus Aurantium Dulcis*) Extract | NATURAL ORANGE EXTRACT #71689/Flavurence | 0.3 |
| Diazolidinyl Urea | GERMALL II/ISP | 0.3 |
| Glycolipids and Hyaluronic Acid | PHYTO/CER HA/Tri-K | 0.3 |
| Palmitoyl Hydroxypropyltrimonium Amylopectin/Glycerin Crosspolymer and Lecithin and grape (*Vitis Vinifera*) Seed Extract | GLYCOSPHERES PCO/Kobo | 0.3 |
| Palmitoyl Hydroxypropyltrimonium Amylopectin/Glycerin Crosspolymer and Lecithin and *Camellia Sinensis* Extract | GLYCOSPHERES GT/Kobo | 0.3 |
| Propylene Glycol | Propylene Glycol/Ashland | 0.6 |
| Algae Extract | HAWAIIAN SEAPLANT EXTRACT-J/Tri-K | 0.2 |
| Lecithin and Tocopherol and Magnesium Ascorbyl Phosphate | OXYSOMES/Barnet | 0.6 |
| Butylene Glycol and Honey Extract (Mel) and Meadowsweet (*Spiraea Ulmaria*) Extract | ACTIPLEX 1072/Active Organics | 1.1 |
| Talc and C9–C13 Fluoroalcohol and Phosphoric Acid | PF-5 TALC JA-46R/Kobo | 0.8 |
| Hydrolyzed Soy Flour | RAFFERMINE/R.I.T.A. | 0.3 |
| Oat (*Avena Sativa*) Protein | REDUCTINE/R.I.T.A. | 0.3 |
| Phytonadione | Phytonadione/Roche | 0.01 |
| Retinol and Polysorbate 20 | RETINOL 50C/BASF | 0.1 |
| *Epilobium Angustifolium* Extract | Canadian Willowherb Whole Extract (5% in water)/Fytokem | 0.5 |
| *Arnica Montana* Extract | ACTIPHYTE OF ARNICA BG50/Active Organics | 0.5 |
| | | 100.0 |

CARPOL ULTREZ 10 is commercially available from B. F. Goodrich Co. of Richfield, OH;
AMIGEL, PHYTO/CER and HAWAIIAN SEA PLANT EXTRACT are available from Tri-K-Chemical of Fairview, MT;
Allantoin and GERMALL II are available from ISP Chemicals Inc. of Calvert City, KY;
DEXPANTHENOL and Phytonadione are available from Roche Holdings, Inc. of Wilmington, DE;
Methylparaben and Propylparaben are commercially available from Ueno Fine Chemicals Inc. of New York, NY
AJIDEW N-50 is commercially available from Ajinomoto USA Inc. of Teaneck, NJ;
BERNEL ESTER is commercially available from Bernel Chemical Co. of Englewood, NJ;
PHYTOLANE is commercially available from Barnet Products Corporation of Englewood Cliffs, NJ;
ARLACEL 60 is commercially available from ICI Americas Inc. of Wilmington, DE;
EMERSOL 132 is commercially available from Henkel Corp. of Hoboken, NJ;
DOW CORNING 200, 350 cs. is commercially available from Dow Corning Corp. of Auburn, MI;
FINSOLV TN is commercially available from Finetex Inc. of Elmwood Park, NJ;
HETOXOL D is commercially available from Heterene Chemical Co. of Paterson, NJ;
NATURAL ORANGE EXTRACT #71689 is commercially available from Flavurence Corp. of Annandale, NJ;
ACTIPLEX 1072 is commercially available from Active Organics Inc. of Lewisville, TX;
PF-5 TALC JA-46R is commercially available from Kobo Products Inc. of South Plainfield, NJ;
RAFFERMINE and REDUCTINE are commercially available from RITA Chemical Corp of East Northport, NY.

The Skin Perfecting Lotion was prepared by metering deionized water into a processing tank and mixing at high speed. CARBOPOL ULTREZ 10 was sprinkled in. When the CARBOPOL ULTREZ 10 was completely dispersed, AMIGEL was added and the mixture mixed until smooth and uniform. The mixture was heated to 80° C., the remaining Part A ingredients were added, and then mixed until uniform. In a separate tank, the Part B ingredients were combined and heated to 80° C. until all the solids were completely dissolved. Part B was added to Part A and the resulting batch was mixed until uniform. Premixed Part C was added and the batch mixed until homogeneous. The batch was cooled to 40° C. and the Part D ingredients were added and mixing continued until the temperature of the mixture was 35° C. The resulting Skin Perfecting Lotion was a light beige, opaque, viscous lotion having a pH at 25° C. of 6.2 to 7.2 and a viscosity of 14,000 to 24,000 cps. (RVT: #5 @10 rpm @25° C.).

Example 4

Acne Management Formula

A pharmaceutical composition according to the invention may be prepared for managing acne as set forth below:

| Ingredients | Trade Name/Supplier | % by weight |
|---|---|---|
| Part A | | |
| Water (Aqua) | Deionized Water | 56.8 |
| Sclerotium Gum | AMIGEL/Alban Muller | 0.4 |
| Disodium EDTA | HAM-ENE NA$_2$/Akzo | 0.3 |
| Allantoin | Allantoin/ISP | 0.2 |
| Methylparaben | Methylparaben/Ueno | 0.3 |
| Zinc Oxide | 66 ZINC OXIDE U.S.P./Whitaker, Clark & Daniels | 0.3 |
| Part B | | |
| Water (Aqua) | Deionized Water | 10 |
| Hydrolyzed Oat Flour and Oat Betaglucan | RITAVENA 5/R.I.T.A. | 2.8 |
| Dicaprylyl maleate | BERNEL ESTER DCM/Bernel | 3 |
| Glycerayl Stearate and PEG-100 Stearate | ARLACEL 165/ICI | 3 |
| Cetearyl Alcohol and Ceteareth-20 | HEXOTOL D/Heterene | 3 |
| Propylparaben | Propylparaben/Ueno | 0.1 |
| Part D | | |
| Salicylic Acid | Salicylic Acid, powder, U.S.P.-N.F./Spectrum | 1.3 |
| Sulfur | Sulfur, precipitated, U.S.P.-N.F./Spectrum | 6.5 |
| Part E | | |
| Water (Aqua) | Deionized Water | 3 |
| Sodium Hydroxide | Sodium Hydroxide, pellets, U.S.P.-N.F./Spectrum | 0.1 |
| Glycolic Acid | GLYPURE 70% GLYCOLIC ACID/DuPont | 6.5 |
| Part F | | |
| Orange (*Citrus Aurantium Dulcis*) Extract | ORANGE EXTRACT PRODUCT #61522/Sunkist | 1.1 |
| Diazolidinyl Urea | GERMALL II/ISP | 0.4 |
| Dipotassium Glycyrrhizate | Dipotassium Glycyrrhizinate/Int'l Sourcing | 0.3 |
| Lecithin and Tocopherol and Magnesium Ascorbyl Phosphate | OXYZOMES/Barnett | 0.3 |
| Palmitoyl | GLYCOSPHERES PCO/Kobo | 0.3 |

| Ingredients | Trade Name/Supplier | % by weight |
|---|---|---|
| Hydroxypropyltrimonium Amylopectin/Glycerin Crosspolymer and Lecithin and Grape (*Vitis Vinifera*) Seed Extract | | |
| | | 100.0 |

AMIGEL is commercially available from Alban Muller International of Vincennes, France;
HAM-ENE NA$_2$ is commercially available from Akzo Chemicals Inc. of Deer Park, TX;
66 ZINC OXIDE U.S.P. is commercially available from Whitaker, Clark & Daniels of South Plainfield, NJ;
Salicylic Acid, powder, U.S.P.-N.F., Sulfur, precipitated, U.S.P.-N.F. and Sodium Hydroxide, pellets, U.S.P.-N.F. are commercially available from Spectrum Mfg. Corp of New Brunswick, NJ;
ORANGE EXTRACT PRODUCT #61522 is commercially available from Sunkist Growers, Inc. of Van Nuys, CA;
Dipotassium Glycyrrhizinate is commercially available from International Sourcing Inc. of Upper Saddle River, NJ.

The Acne Management Formula was prepared by metering deionized water into a processing tank and mixing at high speed. AMIGEL was sprinkled in. When the AMIGEL was completely dispersed, the mixture was heated to 85° C. and the remaining Part A ingredients were added and the mixture mixed well after each addition. In a separate tank, Part B was heated to 100° C., mixed until smooth, cooled to 80° C. and added to the batch. The resulting batch was mixed well. In another tank, the Part C ingredients were heated to 75° C. When all the solids dissolved, Part C was added to the batch, the batch was mixed until smooth and uniform, and the batch cooled to 50° C. Part D ingredients were added to the batch, the batch was homogenized for 5 to 10 minutes until the batch was smooth and uniform, and the batch was cooled to 40° C. The deionized water of part E was premixed with the sodium hydroxide pellets and the resulting solution was mixed well until all solids were dissolved. While mixing the solution, glycolic acid was slowly added in increments and the solution was mixed until homogeneous. The solution was added to the batch and the Part F ingredients were added to the batch. The batch was mixed and cooled to 35° C. The Acne Management Formula was a light yellow, opaque smooth lotion having a pH at 25° C. of 3.8 to 4.8 and a viscosity of 10,000 to 2,000 cps. (RVT: #5 @10 rpm @25° C.).

Example 5

Clarifying Skin Cleanser

A pharmaceutical composition according to the invention may be prepared for managing acne as set forth below:

| Ingredients | Trade Name/Supplier | % by weight |
|---|---|---|
| Part A | | |
| Water (Aqua) | Deionized Water | 48.5 |
| Sodium Lauroyl Oat Amino Acid | PROTEOL O.A.T./Seppic | 2 |
| Decyl Glucoside | ORAMIX NS-10/Seppic | 3 |
| Cocamidopropyl Betaine | AMPHOSOL CA/Stephan | 12.5 |
| Disodium Laureth Sulfosuccinate | MACKANATE EL/McIntyre | 24 |
| PEG-120 Methyl Glucose Dioleate | GLUCAMATE DOE-120/Amerchol | 3.5 |
| Methylparaben | Methylparaben/Ueno | 0.2 |
| PEG-150 Pentaerythrityl Tetrastearate | CROTHIX/Croda | 0.25 |
| Part B | | |
| Salicylic Acid | Salicylic Acid, powder, USP/Spectrum | 2 |
| Tetrasodium EDTA | HAMP-ENE-100/Akzo | 0.3 |
| Triclosan | IRGASAN D300/Ciba Specialty Chemicals | 0.2 |
| Part C | | |
| PPG-26-Buteth-26 and PEG 40 Hydrogenated castor Oil | SOLUBILISANT LRI/ Whittaker, Clark & Daniels | 2 |
| Fragrance | Fragrance-BELL #J7393/Bell | 0.3 |
| Menthol | Menthol Crystals, USP/ Spectrum | 0.1 |
| Part D | | |
| Butylene Glycol and water (aqua) and Black Cohosh (*Cimicifuga Racemosa*) Extract | ACTIPHYTE OF BLACK SNAKEROOT BG50/Active Organics | 0.2 |
| Butylene Glycol and water (aqua) and *Camellia Oleifera* Extract | ACTIPHYTE OF JAPANESE GREEN TEA BG50/Active Organics | 0.2 |
| Sodium PCA | AJIDEW N-50/Ajinomoto | 0.4 |
| Imidazolidinyl Urea | GERMALL 115/ISP | 035 |
| | | 100.0 |

PROTEAL O.A.T. is commercially available from Seppic Inc. of Fairfield, NJ;
AMPHOSOL CA is commercially available from Stephan Co. Inc. of Fort Lauderdale, FL;
GLUCAMATE DOE-120 is commercially available from Amerchol Corp. of Edison, NJ;
HAMP-ENE-100 is commercially available from Akzo Nobel Inc. of Dobbs Ferry, NY;
SOLUBILISANT LRI is commercially available from Whitaker, Clark & Daniels of South Plainfield, NJ;
GERMALL 115 is commercially available from ISP Chemicals Inc. of Calvert City, KY.

The Clarifying Skin Cleanser was prepared by metering deionized water into a processing tank, mixing, and heating to 75° C. The part A ingredients were added and mixed until all the solids dissolved. The resulting mixture was cooled to 60° C. In a separate vessel the Part B ingredients were combined. The Part B ingredients were then added to Part A and the resulting batch was mixed until uniform. The resulting mixture was cooled to 50° C. In a separate vessel the Part C ingredients were mixed until uniform. The part C ingredients were added to the batch and the resulting batch was mixed until uniform. The batch was cooled to 40° C. and the part D ingredients were added and mixing continued until uniform followed by cooling to 30° C. The Clarifying Skin Cleanser Formula was a pale yellow, slightly viscous liquid having a pH at 25° C. of 4.5 to 5.5 and a viscosity of 5,000 to 9,000 cps. (RVT: #@10 rpm @25° C.).

Example 6

Antimicrobial Effectiveness of the Invention—Advanced Acne Prone Skin Formulation Culture Preparation

*Escherichia coli* (ATCC #8739), *Staphylococcus pureus* (ATCC #6533), *Pseudomonas aeruginosa* (ATCC #9027)

were each propagated in Trypicase Soy Broth (TSB) at 35° C. for 24 hrs. *Candida albicans* (ATCC #10231), and *Aspergillus niger* (ATOC #16404) were propagated in Yeast and Mold Broth (YM) at 24° C. for 72 h. One loop of each bacteria culture was streaked onto Trypticase Soy Agar (TSA) and the yeast and mold onto Sabouraud Dextrose Agar (SDA). The bacterial and yeast cultures were incubated for 24 h at 35° C. and 48 h at 24° C., respectively. The mold culture was incubated for 5 days at 24° C. Following appropriate incubation, the surface growth of the organisms were washed with sterile Saline TS. Additional saline was added to reduce the microbial count. Each respective cell suspension was further diluted with sterile saline TS to an appropriate concentration.

Product Inoculation

Five 20-g portions of the Advanced Acne Prone Skin Formula of Example 2 was aseptically placed into sterile bottles. Each bottle was independently inoculated with 0.1 mL of the inoculum suspension.

Target Inoculation Concentration

A final concentration of $10^5$ and $10^6$ cfu/g of product was obtained. This spike suspension was assayed for each respective organism to determine the initial microbial load in the product. All enumeration analyses were performed by preparing serial 10-fold dilutions in Butterfield's Phosphate Buffered Diluent (BPBD), and then plated using the pour plate technique on respective media.

Test Intervals

An enumeration of the target organisms were performed on each inoculum. Immediately after inoculation (less than 1 minute), each product was assayed to determine the density of viable target organisms according to the pour plate technique. Each sample was tested again after 2 and 4 minutes. A 1-g portion was removed and mixed with 9.9 mL of BPBD. Serial dilutions were prepared as appropriate. Test samples containing bacterial cultures were plated with TSA and incubated for 48 h at 35° C. Samples containing yeast and mold were plated with SDA and incubated for 5 days at 24° C.

Results

The following results were obtained for each of the five organisms.

| Testing Schedule (Time: minutes) | Recovery Levels (cfu/g) Advanced Acne Prone Skin Formula |
|---|---|
| Test Organism: *Candida albicans* (ATOC # 10231) Theoretical Inoculum Level: 400,000 cfu/g | |
| 0 (less than 1) | <10 |
| 2 | <10 |
| 4 | <10 |
| Test Organism: *Aspergillus niger* (ATCC # 16404) Theoretical Inoculum Level: 160,000 cfu/g | |
| 0 (less than 1) | <10 |
| 2 | <10 |
| 4 | <10 |
| Test Organism: *Escherichia coli* (ATCC # 8739) Theoretical Inoculum Level: 1,000,000 cfu/g | |
| 0 (less than 1) | <10 |
| 2 | <10 |
| 4 | <10 |

-continued

| Testing Schedule (Time: minutes) | Recovery Levels (cfu/g) Advanced Acne Prone Skin Formula |
|---|---|
| Test Organism: *Staphylococcus aureus* (ATCC # 6538) Theoretical Inoculum Level: 700,000 | |
| 0 (less than 1) | <10 |
| 2 | <10 |
| 4 | <10 |
| Test Organism: *Pseudomonas aeruginosa* (ATCC # 9027) Theoretical Inoculum Level: 260,000 | |
| 0 (less than 1) | <10 |
| 2 | <10 |
| 4 | <10 |

Discussion and Conclusion

The Advanced Acne Prone Skin Formulation prepared according to the present invention exhibited excellent antimicrobial properties. In less than one minute there was greater than a 99.99% reduction in levels of *Candida albicans, Escherichia coli, Staphylococcus aureus, Pseudomonas aeruginosa*, and *Aspergillus niger*.

Example 7

Antimicrobial Effectiveness of Another Formulation of the Invention—Clarifying Skin Cleanser Culture Preparation

*Escherichia coli* (ATCC #8739), *Staphylococcus pureus* (ATCC #6533), and *Pseudomonas aeruginosa* (ATCC #9027) were propagated in Trypicase Soy Broth (TSB) at 35° C. for 24 h. *Candida albicans* (ATCC #10231) and *Aspergillus niger* (ATOC #16404) were propagated in Yeast and Mold Broth (YM) at 24° C. for 72 h. One loop of each bacteria culture was streaked onto Trypticase Soy Agar (TSA) and the yeast and mold onto Sabouraud Dextrose Agar (SDA). The bacterial and yeast cultures were incubated for 24 h at 35° C. and 48 h at 24° C., respectively. The mold culture was incubated for 5 days at 24° C. Following appropriate incubation, the surface growth of the organisms were washed with sterile Saline TS. Additional saline was added to reduce the microbial count. Each respective cell suspension was further diluted with sterile saline TS to an appropriate concentration.

Product Inoculation

Five 20-g portions of the Clarifying Skin Cleanser of Example 1 was aseptically placed into sterile bottles. Each bottle was independently inoculated with 0.1 mL of the inoculum suspension.

Target Inoculation Concentration

A final concentration of $10^5$ and $10^6$ cfu/g of product was obtained. This spike suspension was assayed for each respective organism to determine the initial microbial load in the product. All enumeration analyses were performed by preparing serial 10-fold dilution's in Butterfield's Phosphate Buffered Diluent (BPBD), and then plated using the pour plate technique on respective media.

Test Intervals

An enumeration of the target organisms were performed on each inoculum. Immediately after inoculation (less than 1 minute), each product was assayed to determine the density of viable target organisms according to the pour plate technique. Each sample was tested again after 2 and 4 minutes. A 1-g portion was removed and mixed with 9.9 mL of BPBD. Serial dilutions were prepared as appropriate. Test samples containing bacterial cultures were plated with TSA and incubated for 48 h at 35° C. Samples containing yeast and mold were plated with SDA and incubated for 5 days at 24° C.

Results

The following results were obtained for each of the five organisms.

| Testing Schedule (Time: minutes) | Recovery Levels (cfu/g) Clarifying Skin Cleanser |
|---|---|
| Test Organism: *Candida albicans* (ATOC # 10231) Theoretical Inoculum Level: 400,000 cfu/g | |
| 0 (less than 1) | 25,000 |
| 2 | 20,000 |
| 4 | 14,000 |
| Test Organism: *Aspergillus niger* (ATCC # 16404) Theoretical Inoculum Level: 160,000 cfu/g | |
| 0 (less than 1) | 1,400 |
| 2 | 1,200 |
| 4 | 1,000 |
| Test Organism: *Escherichia coli* (ATCC # 8739) Theoretical Inoculum Level: 1,000,000 cfu/g | |
| 0 (less than 1) | <10 |
| 2 | <10 |
| 4 | <10 |
| Test Organism: *Staphylococcus aureus* (ATCC # 6538) Theoretical Inoculum Level: 700,000 | |
| 0 (less than 1) | <10 |
| 2 | <10 |
| 4 | <10 |
| Test Organism: *Pseudomonas aeruginosa* (ATCC # 9027) Theoretical Inoculum Level: 260,000 | |
| 0 (less than 1) | <10 |
| 2 | <10 |
| 4 | <10 |

Discussion and Conclusion

The Clarifying Skin Cleanser exhibited excellent antimicrobial properties. In less than one minute there was a >99.99% reduction in levels of *Escherichia coli, Staphylococcus aureus*, and *Pseudomonas aeruginosa*. In less than one minute, levels of *Aspergillus niger* and *Candida albicans* were reduced by 99.1% and 94.0%, respectively.

Example 8

Irritation Test Using the Invention

Irritation potential following epidermal contact by compositions prepared according to the invention was examined. Fifty-three subjects ranging from 18 to 77 were evaluated. The patients were administered 0.2 mL, or an amount sufficient to cover the upper back between the scapulae, of a 10 percent dilution of the formulation used in Example 2. The administration occurred by applying the composition to a 1"×¾" absorbent pad portion of an adhesive dressing, which was secured to the treatment site on each patient. The test material remained in contact for a total of 48 hours, and the test sites were evaluated at that time and at 72 hours (24 hours later) for changes using a 6-point scale ranging from no visible skin reaction up to severe erythema, possible edema, vesiculation, bullae and/or ulceration. One test subject did not complete the study. Observations indicated negative irritation throughout the test interval, i.e. no visible skin reaction on a single patient.

Example 9

Hydrogen Peroxide Stability Test

The formulations prepared according to Examples 1 of the invention having hydrogen peroxide, citric acid, salicylic acid, an antibacterial agent, and an amphoteric surfactant were heated to between 40° C. to 45° C. for three months in an oven test. The oxygen content of the formula which was assayed after the stability test, showed no more than 3 weight percent loss of the original hydrogen peroxide content. Such high stability provides an improved composition having a long shelf-life without substantial loss of efficacy.

Examples 10–12

Acne Treatment Regimen

An acne treatment regimen comprising Clarifying Cleanser, Advanced Acne Prone Skin Formula, Skin Perfecting Lotion and Acne Management Formula (Examples 1, 2, 3, and 4, respectively) was administered to 15 subjects. Subjects were evaluated after 2 weeks and 4 weeks use of the treatment regimen. Subjects were evaluated for total facial lesions, skin hydration and overall appearance of acne.

Testing of the Treatment Regimen

The acne treatment regimen comprising a ADVANCED ACNE PRONE SKIN FORMULA, SKIN PERFECTING LOTION, ACNE MANAGEMENT FORMULA, and CLARIFYING SKIN CLEANSER, prepared according to Examples 2, 3, 4, and 5, respectively, was administered to 15 subjects who exhibited a Grade 2–4 acne condition according to the grading scale provided below:

0: Facial skin need not be perfectly clear. A few scattered comedones or papules may be present, but these should be visible only on close examination.

2: About one fourth of facial area is involved, with small papules and large or small comedones. A few pustules or large prominent papules may be present.

4: About half of facial area is involved, with small papules and large or small comedones. A few pustules or large prominent papules are usually present. (If lesions are large, subject may have Grade 4 severity, although less than half of facial area is involved).

6: About three-fourths of facial area is involved, with papules and/or large open comedones. (Lesser facial area of involvement is permissible if inflammatory lesions are large) numerous pustules are usually present, some of which may be large.

8: Practically all of facial area is involved, with lesions. Large prominent pustules are usually visible. Lesions are usually highly inflammatory. Other types of acne (such as conglobata, including sinus and cystic types).

On the first day of the study all subjects were acclimated to ambient temperature and relative humidity for fifteen minutes. After the equilibration period, a trained technician examined each subject's face and recorded the number of inflammatory and non-inflammatory lesions in each of six sections of the face. The lesions of the six sections were totaled to obtain a global assessment score for each subject. Clinical photographs were taken in various poses for each subject and three Corneometer measurements were taken.

Subjects were provided with the treatment regimen and were given the following instructions for the treatment regimen:

CLARIFYING CLEANSER: Apply twice per day (once in the morning and once in the evening). Pour a small amount into hand or wash cloth. Apply to dampened face and neck. Massage gently into full lather. Rinse thoroughly with warm water and pat dry. Follow with ACNE PRONE SKIN FORMULA.

ACNE PRONE SKIN FORMULA: Apply after cleansing twice per daily (once in the morning and once in the evening). Apply a small amount to face and neck or areas affected with acne. Follow with SKIN PERFECTING LOTION.

SKIN PERFECTING LOTION: Use twice per day after cleansing and treating skin. Apply a small amount to face and neck.

ACNE MANAGEMENT FORMULA: Use twice a day after using CLARIFYING CLEANSER, ACNE PRONE SKIN FORMULA, and SKIN PERFECTING LOTION. Apply a small amount to affected area to spot treat.

Subjects were required to maintain a daily diary indicating date, time of use and comments. Subjects were permitted to use their customary make-up products during the study. However, subjects were instructed not to introduce any new cosmetic or facial treatment products during the study. Following the two week test material use period subjects were evaluated for an interim count of total facial lesions, Corneometer readings and clinical photographs. After four weeks of test material use subjects returned with their diaries for a final lesion count, Corneometer readings and clinical photographs. Standard paired t-tests were used to determine statistically significant differences between baseline and two (2) and four (4) week total facial lesion counts and Corneometer readings. Statistical significance exists for all p-values less than or equal to 0.05 at the 95% confidence level. Improvement scores for the appearance of acne in clinical photographs were analyzed using Z-tests.

A total of fourteen subjects finished the study. One subject was disqualified immediately for lack of compliance with the Inclusion Criteria of the protocol. A review of the daily diaries indicated that four (4) subjects reported redness, burning, stinging and/or "irritation" during the study period. One (1) of the subjects reported the onset of redness and burning on day five (5) of the study immediately after product application and lasting for fifteen (15) to twenty (20) minutes. The subject was instructed to discontinue test material use on day ten (10) of the study. On day fourteen (14) the subject was examined by a doctor and no evidence of skin irritation was observed. The subject was instructed to begin use of the treatment material at this time. The subject reported no evidence of irritation until day twenty four (24) of the study and completed study participation. No evidence of irritation was observed at the final visit. The subjects reaction was diagnosed as dermatitis. The remaining subjects reported symptoms following one (1) to two (2) uses of the test material and completed study participation without further complaints.

Example 10

Total Lesion Count Following Treatment Regimen

The acne present on the skin of each subject was evaluated by visual examination using the grading scale described herein. The number of lesions on the face were counted at each visit. The number of open and closed comedones, as well as papules and pustules, were recorded. A global assessment score, the total of all lesions, was recorded for each visit. Reductions in the global assessment score are indicative of a reduced incidence and/or severity of acne lesions. The data for total lesion count is provided below.

| | Total Lesion Count | | |
|---|---|---|---|
| | Baseline | 2 Weeks | 4 Weeks |
| Mean | 44.4 | 33.4 | 27.6 |
| Mean Percent Difference from Baseline | | −26% | −40% |
| σ | | 30% | 22% |

The regimen showed a statistically significant decrease of twenty-six percent (26%) in the number of lesions observed after using the treatment regimen for two (2) weeks and a statistically significant decrease of forty (40%) after using the treatment regimen for four (4) weeks compared to baseline ($p=0.02$ and $p=1.07$ E-05, respectively).

Example 11

Photographic Evaluation Following Treatment Regimen

Photographs of subjects were taken at designated visits using the Canfield Clinical System of imaging equipment. This particular system permits comparison of photographs to be made with the confidence that the only factors which may have changed are those resulting from treatment. This is achieved by precisely and reproducibly positioning the head of the subject and carefully controlling the lighting, film type and processing. Photographs were visually assessed and evaluated by a trained technician before and after use of the test material. The following scoring scale was used for visual assessment of the skin:

1=no improvement
2=slight improvement
3=mild improvement
4=moderate improvement
5=extreme improvement Improvement scores for the appearance of acne in clinical photographs were analyzed using Z-tests. For the two (2) and four (4) week scores, the number of subjects exhibiting improvements scoring a two (2), three (3), four (4) or five (5) was compared to the number of subjects exhibiting no improvement, scored as a one (1). The improvement assessment of the overall appearance of acne, rated from clinical photographs, is provided below.

| | Photographic Evaluation | | | | | |
|---|---|---|---|---|---|---|
| | Score: | 1 | 2 | 3 | 4 | 5 |
| Week 2 | Number of Subjects Assigned each Score | 5 | 5 | 2 | 2 | 0 |

-continued

| | Photographic Evaluation | | | | | |
|---|---|---|---|---|---|---|
| | Score: | 1 | 2 | 3 | 4 | 5 |
| | Percentage | 35.7% | | 64.3% | | |
| | Z-Score | | | −1.12 | | |
| Week 4 | Number of Subjects Assigned each Score | 4 | 4 | 5 | 1 | 0 |
| | Percentage | 28.6% | | 71.4% | | |
| | Z-Score | | | −1.77 | | |

The number of subjects exhibiting improvement from baseline in the overall appearance of acne at two (2) weeks was greater than subjects with no improvement. The Z-score obtained at two (2) weeks corresponds to improved skin appearance having a statistical significance at a 74% confidence level. In the four (4) week photograph the number of subjects exhibiting improvement from baseline in the overall appearance of acne was greater than subjects with no improvement. The Z-score obtained at four (4) weeks corresponds to improved skin appearance having statistical significance at a 92% confidence level.

Example 12

Moisturization via Corneometer Following Treatment Regimen

Changes in skin hydration were measured with a CORNEOMETER which is a commercially available instrument (CM-820, Courage and Khazaka Germany) designed to measure changes in the capacitance of the skin resulting from small changes in the degree of hydration. The CORNEOMETER expresses the capacitance of the skin in arbitrary unit of skin hydration (H). The instrument is capable of measuring the moisture of the stratum corneum to a depth of 0.1 mm and is used to measure the effects of cosmetic preparations on the moisture content of the skin. Tests using the CORNEOMETER were conducted by taking 3 measurements, one at the right and left cheek and one at the center of the skin, for each subject. The three measurements were then averaged for each subject. The data for skin hydration (H) is provided below.

| Skin Hydration (H) | | | |
|---|---|---|---|
| | Baseline | 2 Weeks | 4 Weeks |
| Mean | 70.8 | 51.6 | 49.5 |
| Mean Percent Difference from Baseline | | −26% | −29% |
| σ | | 14% | 12% |

The regimen showed a statistically significant decrease in Skin Hydration, H, of twenty-six percent (26%) after using the treatment regimen for two (2) weeks and a statistically significant decrease of twenty-nine (29%) after using the treatment regimen four (4) weeks compared to baseline ($p = 2.27\text{ E}{-}05$ and $p = 5.38\text{ E}{-}06$, respectively). A loss in skin hydration is typically observed following treatment with anti-acne products.

Example 13

Skin Cleanser of Invention with Antifungal and Antibacterial Agents

A pharmaceutical composition according to the invention may be prepared for cleansing skin as set forth below:

| Ingredient | Trade Name/Supplier | % by Weight |
|---|---|---|
| Part A | | |
| Deionized Water | N/A | 50 |
| Trisodium Ethylene-Diamine-Tetraacetic Acid (EDTA) | HAMP-ENE Na$_3$T/Akzo Nobel | 0.2 |
| Sodium Laureth-13 Carboxylate | SURFINE WLL/Finetex | 10 |
| Disodium Laureth Sulfosuccinate | MACKANATE EL/McIntyre Group | 17 |
| Disodium Cocoamphodiacetate | MONATERIC CDX-38/Mona | 11 |
| PEG-150 Pentaerythrityl Tetrastearate | CROTHIX/Croda | 1.5 |
| PEG-150 Distearate | KESSCO PEG 6000 DS/Stepan | 0.7 |
| Methylparaben | N/A | 0.2 |
| Part B | | |
| Clotrimazole | N/A | 0.8 |
| Citric Acid | N/A | 1.5 |
| Triclosan | IRGASAN DP300/Ciba | 0.3 |
| Part C | | |
| PPG-26-Buteth-26, PEG-40 Hydrogenated Castor Oil | SOLUBILISANT LR1/Les Colorant Wackherr SA | 2 |
| Fragrance (Parfum) | Fragrance-BELL #J7393/Bell Flavors and Fragrances | 0.3 |
| Menthol | Menthol Crystals, USP | 0.1 |
| Part D | | |
| Butylene Glycol, Deionized water, Black Cohosh (Cimicifuga Racemosa) Extract | ACTIPHYTE OF BLACK SNAKEROOT BG50/Active Organics | 0.1 |
| Butylene Glycol, Deionized water, Camellia Oleifera Extract | ACTIPHYTE OF JAPANESE GREEN TEA BG50/Active Organics | 0.1 |
| Sodium Peroxylinecarbolic Acid (PCA) | AJIDEW-50/Ajinomoto | 0.2 |
| Cocamidopropyl PG-Dimonium Chloride Phosphate | PHOSPHOLIPID PTC/Mona | 1 |
| Part E | | |
| Hydrogen Peroxide | Hydrogen Peroxide, 35% solution, technical | 3 |
| | | 100% |

Deionized water was metered into the processing tank and mixing subsequently begun. The water was heated to 75° C. and the remainder of Part A was added and mixed until uniform. The mixture was cooled to 60° C. and the Part B ingredients were added and mixed until uniform. The mixture was then cooled to 50° C. In a separate vessel, Part C was premixed until uniform and then added to the mixture of Parts A and B. Parts A, B, and C were mixed until uniform and cooled to 40° C. The Part D ingredients were added and mixed until uniform, then cooled to 30° C. Part E was added and mixed until uniform, resulting in a colorless, clear, slightly viscous fluid having a pH at 25° C. of between 4 to 6 and a viscosity between 3,000 to 4,000 cps (RVT: #4 @10 rpm @25° C.).

| Ingredient | Trade Name/Supplier | % by Weight |
|---|---|---|
| Part A | | |
| Deionized Water | N/A | 50 |
| Trisodium Ethylene-Diamine-Tetraacetic Acid (EDTA) | HAMP-ENE Na₃T/Akzo Nobel | 0.2 |
| Sodium Laureth-13 Carboxylate | SURFINE WLL/Finetex | 10 |
| Disodium Laureth Sulfosuccinate | MACKANATE EL/McIntyre Group | 17 |
| Disodium Cocoamphodiacetate | MONATERIC CDX-38/Mona | 11 |
| PEG-150 Pentaerythrityl Tetrastearate | CROTHDIX/Croda | 1.5 |
| PEG-150 Distearate | KESSCO PEG 6000 DS/Stepan | .7 |
| Methylparaben | N/A | 0.2 |
| Part B | | |
| Ciclopirox Olamine | N/A | 0.8 |
| Citric Acid | N/A | 1.5 |
| Triclosan | IRGASAN DP300/Ciba | 0.3 |
| Part C | | |
| PPG-26-Buteth-26, PEG-40 Hydrogenated Castor Oil | SOLUBILISANT LRl/Les Colorant Wackherr SA | 2 |
| Fragrance (Parfum) | Fragrance - BELL #J7393/ Bell Flavors and Fragrances | 0.3 |
| Menthol | Menthol Crystals, USP | 0.1 |
| Part D | | |
| Butylene Glycol, Deionized water, Black Cohosh (*Cimicifuga Racemosa*) Extract | ACTIPHYTE OF BLACK SNAKEROOT BG50/Active Organics | 0.1 |
| Butylene Glycol, Deionized water, *Camellia Oleifera* Extract | ACTIPHYTE OF JAPANESE GREEN TEA BG50/Active Organics | 0.1 |
| Sodium Peroxylinecarbolic Acid (PCA) | AJIDEW-50/Ajinomoto | 0.2 |
| Cocamidopropyl PG-Dimonium Chloride Phosphate | PHOSPHOLIPID PTC/Mona | 1 |
| Part E | | |
| Hydrogen Peroxide | Hydrogen Peroxide, 35% solution, technical | 3 |
| | | 100% |

Deionized water was metered into the processing tank and mixing subsequently begun. The water was heated to 75° C. and the remainder of Part A was added and mixed until uniform. The mixture was cooled to 60° C. and the Part B ingredients were added and mixed until uniform. The mixture was then cooled to 50° C. In a separate vessel, Part C was premixed until uniform and then added to the mixture of Parts A and B. Parts A, B, and C were mixed until uniform and cooled to 40° C. The Part D ingredients were added and mixed until uniform, then cooled to 30° C. Part E was added and mixed until uniform, resulting in a colorless, clear, slightly viscous fluid having a pH at 25° C. of between 4 to 6 and a viscosity between 3,000 to 4,000 cps (RVT: #4 @10 rpm @25° C.).

Various modifications of the invention in addition to those shown and described herein will be apparent to those skilled in the art from the foregoing description. Such modifications are also intended to fall within the scope of the appended claims. The foregoing disclosure includes all the information deemed essential to enable those skilled in the art to practice the claimed invention.

What is claimed is:

1. A skin cleansing pharmaceutical composition comprising:
   an acidic component comprising a hydroxy acid or tannic acid, or a pharmaceutically acceptable salt thereof, present in an amount greater than about 4 weight percent sufficient to exfoliate at least a portion of the skin;
   hydrogen peroxide in an amount sufficient to cleanse the skin without substantial irritation thereof; and
   metronidazole.

2. The pharmaceutical composition of claim 1, wherein the composition further comprises a pharmaceutically acceptable carrier or excipient.

3. The pharmaceutical composition of claim 1, wherein the acidic component comprises an alpha-hydroxy acid, beta-hydroxy acid, or tannic acid.

4. The pharmaceutical composition of claim 3, wherein the acidic component comprises glycolic acid, lactic acid, citric acid, salicylic acid, or tannic acid.

5. The pharmaceutical composition of claim 1, further comprising an amount of amphoteric surfactant and an amount of citric acid sufficient to inhibit hydrogen peroxide decomposition for at least three months.

6. The pharmaceutical composition of claim 5, wherein the amount of amphoteric surfactant and citric acid is sufficient to inhibit hydrogen peroxide decomposition at 40° C. for at least three months.

7. The pharmaceutical composition of claim 1, wherein the acidic component is present in an amount from about 4 to 12 weight percent, the hydrogen peroxide is present in an amount from about 0.01 to 6 weight percent, and the metronidazole is present in an amount from about 0.01 to 1.5 weight percent, of the composition.

8. The pharmaceutical composition of claim 1, further comprising at least one of a surfactant, a stabilizer, a preservative, a moisturizer, anti-inflammatory agent, anti-oxidant, or a coloring agent, which together may be present in an amount from about 10.1 to 99.1 weight percent of the composition.

9. A gel, paste, cream, lotion, emulsion, or ointment comprising the pharmaceutical composition of claim 1.

* * * * *

UNITED STATES PATENT AND TRADEMARK OFFICE
CERTIFICATE OF CORRECTION

PATENT NO. : 7,018,660 B2
APPLICATION NO. : 10/093443
DATED : March 28, 2006
INVENTOR(S) : H. Murad It is certified that error appears in the above-identified patent and that said Letters Patent is hereby corrected as shown below:

At col. 4, line 1, replace "olaimine" with --olamine--.

At col. 6, line 65, replace "tricomona" with --trichomona--.

At col. 7, line 8, replace "olaimine" with --olamine--; line 12, replace "sulfacetamde" with --sulfacetamide--;
Line 15, replace "loemfloxacin" with --lomefloxacin--.

At col. 10, line 17, replace "meglumaine" with --meglumine--.

At col. 18, line 66, replace "*pureus*" with --*aureus*--.

At col. 19, lines 1 and 5, replace "Trypicase" with --Trypticase--.

At col. 20, line 34, replace "*pureus*" with --*aureus*--.

Signed and Sealed this

Nineteenth Day of September, 2006

JON W. DUDAS
*Director of the United States Patent and Trademark Office*